United States Patent [19]

Craig et al.

[11] Patent Number: 5,064,484
[45] Date of Patent: Nov. 12, 1991

[54] METHOD OF FORMING AND BONDING FLUFF PADS

[75] Inventors: Grantland A. Craig; Gary E. Johnson, both of Green Bay, Wis.

[73] Assignee: Paper Converting Machine Company, Green Bay, Wis.

[21] Appl. No.: 561,975

[22] Filed: Aug. 2, 1990

Related U.S. Application Data

[63] Continuation-in-part of Ser. No. 297,482, Jan. 17, 1989, abandoned.

[51] Int. Cl.⁵ .................................................. B32B 5/02
[52] U.S. Cl. ................................. 156/62.6; 156/62.2; 156/296; 264/121; 264/126; 425/80.1; 425/81.1
[58] Field of Search ................. 156/296, 62.2, 62.4, 156/62.6; 264/121, 125, 126; 425/82.1, 83.1, 80.1, 81.1; 19/301, 302, 304, 308

[56] References Cited

U.S. PATENT DOCUMENTS

| | | | |
|---|---|---|---|
| 2,544,019 | 3/1951 | Heritage | 264/121 |
| 2,714,081 | 7/1955 | Burgon | 264/121 X |
| 3,501,369 | 3/1970 | Drelich | 428/288 |
| 3,619,322 | 11/1971 | Fleissner | 156/62.2 |
| 3,939,240 | 2/1976 | Savich | 264/335 X |
| 4,201,499 | 8/1965 | Casse | 425/81.1 X |
| 4,540,454 | 9/1985 | Pieniak et al. | 156/296 |
| 4,592,708 | 6/1986 | Feist | 264/121 X |
| 4,666,647 | 5/1987 | Enloe | 264/121 |

OTHER PUBLICATIONS

Thermally Bonded Cores Add Value to Absorbent Products, *Absorbent Products*, Jan.-Feb. 1988.

*Primary Examiner*—Michael W. Ball
*Assistant Examiner*—Michele K. Yoder
*Attorney, Agent, or Firm*—Tilton, Fallon, Lungmus & Chestnut

[57] ABSTRACT

A method of forming and bonding fluff pads for diapers and the like wherein both the steps of forming and bonding are performed on the same vacuum drum.

4 Claims, 2 Drawing Sheets

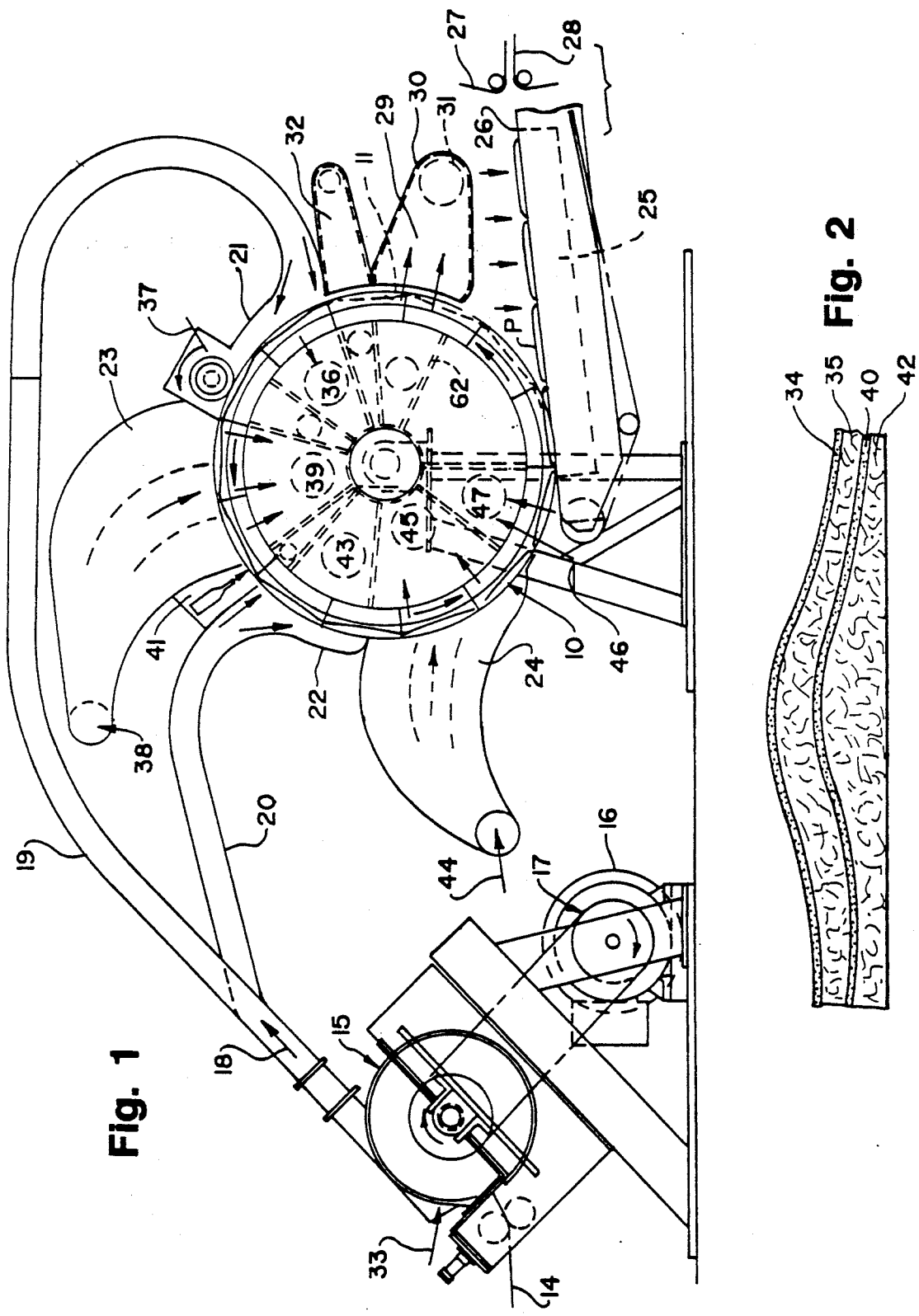
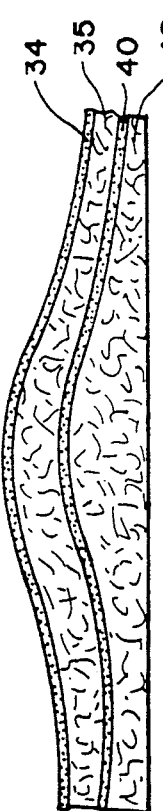

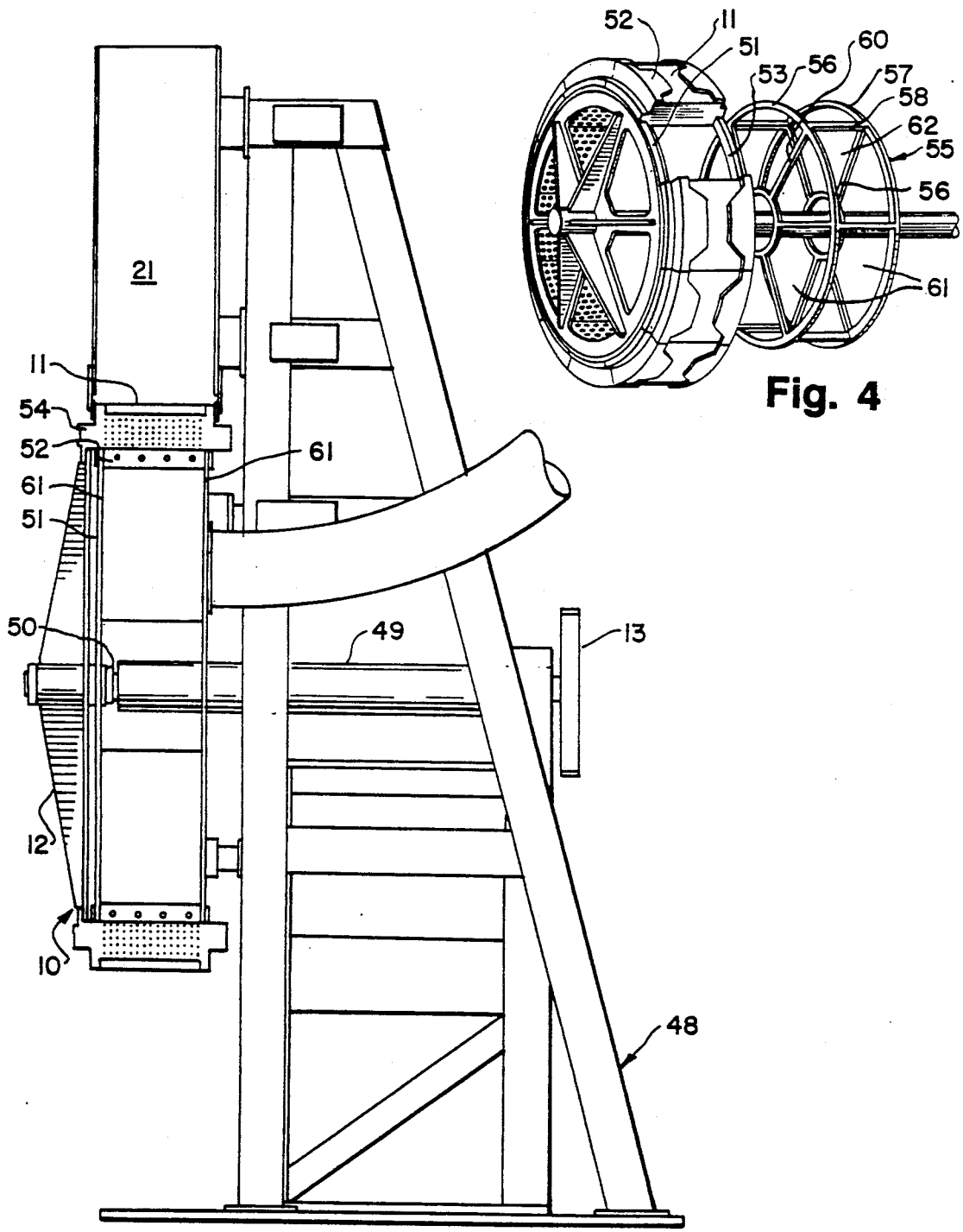

METHOD OF FORMING AND BONDING FLUFF PADS

This application is a continuation-in-part of our co-pending application, Ser. No. 297,482 filed Jan. 17, 1989 now abandoned.

BACKGROUND AND SUMMARY OF INVENTION

This invention relates to a method of forming and bonding fluff pads for diapers and the like, and more particularly, to a method employing an annular drum which achieves both pad formation and thermal bonding on one vacuum drum.

Fluff forming drums have been known for a considerable time—see, for example, co-owned U.S. Pat. No. 3,599,293. Further, both the processes of pad formation and thermal bonding are existing art, yet no one has performed both on a single drum.

A significant product advantage accrues from the invention which performs both of these processes on a single drum—as compared to the separate processes. This advantage resides in retaining the shape of the pad. Diaper producers have expended much effort in developing pad shapes to achieve optimum performance in the take-up of excreta. Yet, the very step of removing the pad from the forming drum distorts the shape. Thus, the bonding step introduces more distortions into the now-unconfirmed pad.

A significant operational advantage resides in the better control of air flows (both forming and bonding) because these can be segmented on the drum. More particularly, these advantages (and others) can be tabulated as follows:

1. Removal of the pad—because of the increased bonding possible with the synthetic fluff mixture, the pads may be removed from the forming molds more cleanly.
2. Integrity of the pad—because the pads are bonded in the forming mold, the initial formation has not been disturbed by handling. This provides the largest amount of fiber entanglement possible and, hence, the greatest bonded fiber areas. It will be appreciated that handling such as bending or extension/compression of the pad tends to dislodge the fiber bonds established in the forming process.
3. Simplicity of mechanism—one drum may be used for both processes thereby eliminating intermediate transfer mechanisms.
4. Cost savings—with the inventive method it is possible to eliminate the tissue overwrap usually present to assist in transporting the pad to the point of insertion into the final product, i.e., disposable diaper, sanitary pad, etc.

The basic process includes first converting wood pulp or other fibrous materials and the bonding polyolefin into fibers suspended in air via a hammermill or other fiberizer. These suspended fibers, called fluff blend, are then collected on a screen surface which allows the air to pass through while retaining the fluff blend.

The screen consists of woven or other formaminous material which has a significantly open area (to air flow) and is formed in the shape of the desired pad. These screen areas or pocket means are supported on a rotating drum through which the air is exhausted.

Pad formation may take place in several steps consisting of fluff blend deposits, additive deposits such as super-absorbents, and scarfing. Scarfing refers to the process of brushing the outside surface of the newly formed pad with a rotating brush roll or similar aggressive surface. These steps may be repeated to form multiple layers of materials in the pad.

The formed pads then continue rotating on the drum into an area where hot air is directed through the pads and exhausted from the drum interior. At least a portion of the pad contains synthetic fibers, i.e., the polyolefin fibers of a melting point lower than the natural (wood) fibers which constitute the majority of the pad. By heating the pad to the melting point of the synthetic fibers but below the wood fibers, the synthetic fibers can be made to melt and "wick" to the wood fibers. Once heated to the bonding temperature, the pads are cooled causing the molten materials to solidify and bond the fiber structure together to achieve the advantages outlined above. The concurrent forming and bonding on a forming drum to provide an undistorted diaper pad is not taught by the prior art, viz., U.S. Pat. Nos. 2,544,019; 2,714,081; 3,201,499; 3,051,369; 3,619,322; 3,939,240; 4,592,708 and 4,666,647.

Other advantages and objects of the invention may be seen in the details of the ensuing specification.

BRIEF DESCRIPTION OF THE DRAWINGS

The invention is described in conjunction with an illustrative embodiment, in which FIG. 1 is a fragmentary side elevational view, essentially schematic, drum apparatus constructed according to the teachings of this invention;

FIG. 2 is an enlarged longitudinal sectional view, also somewhat schematic, of one of the diaper pads of FIG. 1;

FIG. 3 is a fragmentary end elevational view of the apparatus of FIG. 1; and

FIG. 4 is a perspective, exploded view, partially schematic of the forming drum of the apparatus.

DETAILED DESCRIPTION

In the illustration given and with reference to first to FIG. 1, the numeral 10 designates generally the pad forming drum which is seen to support a plurality of circumferentially spaced pockets 11 in the outer peripheral surface thereof. Normally, the drum has a diameter of 8 to 10 feet. In the illustration given, the drum, for simplicity, is illustrated only "one wide". However, it will be appreciated that a number of pockets may be disposed in axially aligned relation. The drum 10, along one side is equipped with a spider 12 to provide means for connecting a drive generally designated 13 and which rotates the drum (See FIG. 3).

Referring again to FIG. 1, a pulp blend of wood fiber and polyolefin is introduced as at 14 into a hammermill generally designated 15. The hammermill 15 is rotated by means of a motor 16 through a drive generally designated 17. The fiberized fluff blend designated by the arrow 18 is forced through ducts 19, 20 into plenums 21, 22 which extend partially circumferentially around the drum 10. Heated air is introduced through plenums 23, 24 and the formed pads P are withdrawn from the drum under vacuum applied by the vacuum box 25 onto a conveyor 26. Thereafter, the pads P are enveloped between webs of non-woven and polyethylene as at 27 and 28.

After the pads have been removed, the now-empty pockets 11 are cleaned by virtue of air being drawn radially outward as at 29 in the vacuum hood 30. A pipe 31 is connected to a vacuum source (not shown). Immediately thereafter a release powder is applied through a plenum 32 to the still-empty pockets 11.

It is believed that a specific example of the operation of the invention will be helpful in the understanding thereof.

EXAMPLE

The web 14 (see the left hand portion of FIG. 1) in this example is a pulp blend consisting of 85% wood fiber and 15% olefin and is introduced in the amount of 2,400 pounds per hour. A suitable pulp blend is available from Hercules, Inc. under the designation PULPEX E-338. Air at room temperature, viz., 70° F., is also drawn in to the hammermill 15 in the amount of 3,000 CFM which is illustrated schematically as at 33.

The first layer of material laid down in the pockets 11 is the fluff release agent from the plenum 32 and this is designated schematically in FIG. 2 by the numeral 34. Next, the fluff blend being transported in the duct 19 to the plenum 21 is laid down to form a layer 35 with the air exiting through an exhaust port 36. This first layer 35 is subjected to scarfing as at 37.

Bonding of the first layer 35 is achieved by heated air entering the plenum 23 as at 38 in the amount of about 1,000 CFM at about 320° F. This air exits through port 39 at about 210° F. Next, a layer of super absorbent powder schematically represented in FIG. 2 by the numeral 40 is laid down in the area occupied by the plenum 41.

A second fluff blend layer 42 (see FIG. 2) is laid down through the plenum 22 with the air exiting through the port 43. Thereafter, bonding occurs with the heated air in the plenum 24 entering as at 44 in the amount of 1,000 CFM at 350° F. and exiting through the port 45 at a temperature of about 250° F.

Cooling air as at 46 is introduced to the last sector of the forming drum 10 and exhausts through the port 47.

FORMING DRUM STRUCTURE

Referring to FIG. 3, it will be seen that the forming drum 10 is supported upon a frame generally designated 48. The frame 48 has releasably clamped thereto a translation tube 49 which rotatably carries a shaft 50 to which spire 12 is attached. For greater details on the construction of the drum 12 reference can be made to co-owned U.S. Pat. No. 4,995,141.

The spider 12 carries a ring 51, a plurality of pad forms 52 (which define the pockets 11), and through the pad forms, a second ring 53—see also FIG. 4. Thus, the inboard ring 53 is connected only to the ring 51 via the arcuately shaped pad forms 52. The pad forms 52 are equipped on both sides with clamps as at 54 (see the central left hand portion of FIG. 3) which fix the rings 51, 53 together.

Fitted within the drum 10—more particularly, the axially spaced rings 51, 53 is a stationary plenum generally designated 55 (see FIG. 4). This is fixedly mounted on the frame 48 and is sealingly related to the drum rings 51, 53.

More particularly, the inner plenum 55 includes a generally cylindrical structure defined by rings 56 and 57 which are integrated together by means of transverse and radially extending members as at 58, 59 and 60. Fitted within the rings as at 61 are annular plates closing the plenum and which are advantageously constructed of transparent material such as plexiglass. Further, sector-forming plates as at 62 are provided within the radially extending members 59, 60 and the axially extending member 58.

Now referring to FIG. 1, it will be seen that a number of sector-forming plates are provided as at 62. Thus, a sector-shaped chamber is provided for each one of the outer plenums 21–24, 29 and 32. No plenum is necessary for reducing the cooling air 46 which is at room temperature and which is drawn in under the influence of the exhaust port 47.

SUMMARY OF OPERATION

A web 14 which advantageously includes both wood pulp and polyolefin is introduced into the hammermill 15. Room temperature air is also drawn into the hammermill as at 33 with the fluff blend being delivered simultaneously to the plenums 21 and 22. The fibers are deposited in pockets 11 (see FIG. 4) with the air flowing radially inwardly under the plenum 21 and being exhausted through port 36.

Next, heated air to provide the bonding function is introduced through the plenum 2 and exhausted through the port 39. Super absorbent powder may be added at this stage at the station 41 to provide the layer 40—see FIG. 2.

Another layer of fluff blend 42 is developed by the fibers issuing from the plenum 22 and exiting through the exhaust port 43. Bonding of these fibers is achieved by heated air flowing radially inwardly from the plenum 24. Thereafter, the pad is cooled by air as at 56, removed onto the conveyor 26 under the influence of vacuum as at 25 for further processing as with the polyethylene and non-woven webs 27, 28. The pockets 11 are then cleaned by air flowing radially outwardly into the plenum 29 under the influence of vacuum as at 31. The still empty pockets 11 are then coated with a release material 34 (see FIG. 2) by virtue of the plenum 32.

While in the foregoing specification, a detailed description of an embodiment of the invention has been set down for the purpose of illustration, many variations in the details herein given may be made by those skilled in the art without departing from the spirit and scope of the invention.

We claim:

1. A method of developing an absorbent fluff pad for a diaper comprising:
   providing an annular drum having circumferentially-spaced pad-forming, formaminous pocket means in the peripheral surface thereof,
   flowing an air stream containing synthetic binder-equipped fluff fibers radially inwardly of said surface through a first sector of said drum to deposit said fiber sequentially in each pocket means while rotating said drum,
   heating air to a temperature above the melting point of said binder and flowing said heated air radially inwardly of said drum through a second sector subsequent in the direction of drum rotation to said first sector to thermally bond said synthetic binder to unify said fluff fibers, repeating said steps of depositing and heating and
   removing the pads from said drum.

2. The method of claim 1 including the step of flowing air through a third sector to cool said pads.

3. The method of claim 1 including the step of scarfing said pads before subjecting the same to heated air.

4. The method of claim 1 including the step of initially flowing an air stream of release material into a sector prior to said fist sector to provide a binder-free layer in said pocket means.

* * * * *